United States Patent
Hattori et al.

(10) Patent No.: US 10,453,192 B2
(45) Date of Patent: Oct. 22, 2019

(54) CYTOLOGIC DIAGNOSIS SUPPORT APPARATUS, CYTOLOGIC DIAGNOSIS SUPPORT METHOD, REMOTE DIAGNOSIS SUPPORT SYSTEM, SERVICE PROVIDING SYSTEM, AND IMAGE PROCESSING METHOD

(71) Applicant: HITACHI HIGH-TECHNOLOGIES CORPORATION, Tokyo (JP)

(72) Inventors: Hideharu Hattori, Tokyo (JP); Yasuki Kakishita, Tokyo (JP); Kenko Uchida, Tokyo (JP); Sadamitsu Aso, Tokyo (JP); Fumiaki Hamazato, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 96 days.

(21) Appl. No.: 15/556,546

(22) PCT Filed: Jan. 28, 2016

(86) PCT No.: PCT/JP2016/052426
§ 371 (c)(1),
(2) Date: Sep. 7, 2017

(87) PCT Pub. No.: WO2016/152242
PCT Pub. Date: Sep. 29, 2016

(65) Prior Publication Data
US 2018/0053296 A1 Feb. 22, 2018

(30) Foreign Application Priority Data
Mar. 25, 2015 (JP) ................. 2015-063103

(51) Int. Cl.
*G06K 9/00* (2006.01)
*G06T 7/00* (2017.01)
(Continued)

(52) U.S. Cl.
CPC ....... *G06T 7/0012* (2013.01); *G01N 33/4833* (2013.01); *G06K 9/4604* (2013.01);
(Continued)

(58) Field of Classification Search
CPC ......... G06T 7/0012; G06T 2207/30024; G06T 2207/20081; G06T 2207/10056;
(Continued)

(56) References Cited

U.S. PATENT DOCUMENTS 6,418,238 B1 * 7/2002 Shiratani ............... G06T 7/0012
382/128
8,787,636 B2 7/2014 Marugame
(Continued)

FOREIGN PATENT DOCUMENTS

JP 2006-517663 A 7/2006
JP 2009-180539 A 8/2009
(Continued)

OTHER PUBLICATIONS

The Japanese Office Action dated Jan. 9, 2018 for the Japanese Application No. 2015-063103.
(Continued)

*Primary Examiner* — Andrew M Moyer
(74) *Attorney, Agent, or Firm* — Volpe and Koenig, P.C.

(57) ABSTRACT

The present invention realizes determination of tissues and cells from an image by calculating feature values of a deformed degree of the cells even in a case where the tissues or the cells have various shapes. An image diagnosis support apparatus according to the present invention executes processing of inputting an image of cells, processing of extracting the feature values of a plurality of direction components from a target image of the processing, processing of determining whether or not the image corresponds to one-classification by using the plurality of feature values, and
(Continued)

(a)

(b) ① NORMAL CELLS (UNIFORM SHAPE)

(c)

(d) ② ABNORMAL CELLS (UNUNIFORM SHAPE)

processing of determining whether or not the determination processing is finished with respect to all of the classifications set in advance (FIG. 1).

9 Claims, 12 Drawing Sheets

(51) Int. Cl.
    *G01N 33/483*     (2006.01)
    *G06K 9/46*     (2006.01)
    *G06K 9/62*     (2006.01)

(52) U.S. Cl.
    CPC .. *G06K 9/6267* (2013.01); *G06T 2207/10056* (2013.01); *G06T 2207/10088* (2013.01); *G06T 2207/10132* (2013.01); *G06T 2207/20081* (2013.01); *G06T 2207/30024* (2013.01); *G06T 2207/30096* (2013.01)

(58) Field of Classification Search
    CPC . G06T 2207/30096; G06T 2207/10132; G06T 2207/10088; G01N 33/4833; G06K 9/6267; G06K 9/4604
    USPC .................................................. 382/128–134
    See application file for complete search history.

(56) References Cited

U.S. PATENT DOCUMENTS

| | | |
|---|---|---|
| 9,384,550 B2 | 7/2016 | Mimura et al. |
| 2006/0083418 A1 | 4/2006 | Watson et al. |
| 2009/0190821 A1 | 7/2009 | Marugame |
| 2011/0170754 A1* | 7/2011 | Yoshihara ............. G06T 7/0012 382/128 |
| 2014/0072193 A1* | 3/2014 | Motomura ............ G06T 7/0012 382/128 |
| 2015/0324997 A1 | 11/2015 | Murakami |
| 2016/0242742 A1* | 8/2016 | Gratacos Solsona ....................... A61B 8/0808 |

FOREIGN PATENT DOCUMENTS

| | | |
|---|---|---|
| JP | 2010-203949 A | 9/2010 |
| JP | 2014132433 A2 | 7/2014 |
| JP | 2015-114172 A | 6/2015 |
| WO | 2010/041423 A1 | 4/2010 |
| WO | 2013/076927 A1 | 5/2013 |
| WO | 2015/145643 A1 | 10/2015 |

OTHER PUBLICATIONS

International Search Report for 2016/152242 A1, dated May 10, 2016.

Extended European Search Report dated Sep. 19, 2018 for the European Patent Application No. 16768145.1.

Gao et al., "HEp-2 Cell Image Classification with Convolutional Neural Networks," 2014 1st Workshop on Pattern Recognition Techniques for Indirect Immunofluorescence Images, Stockholm, pp. 24-28 (2014).

Keskin et al., "Image Classification of Human Carcinoma Cells Using Complex Wavelet-Based Covariance Descriptors," PLOS | ONE (Jan. 16, 2013).

Nguyen et al., "Prostate cancer detection: Fusion of cytological and textural features." Journal of pathology informatics (2011).

* cited by examiner

[Fig. 1]
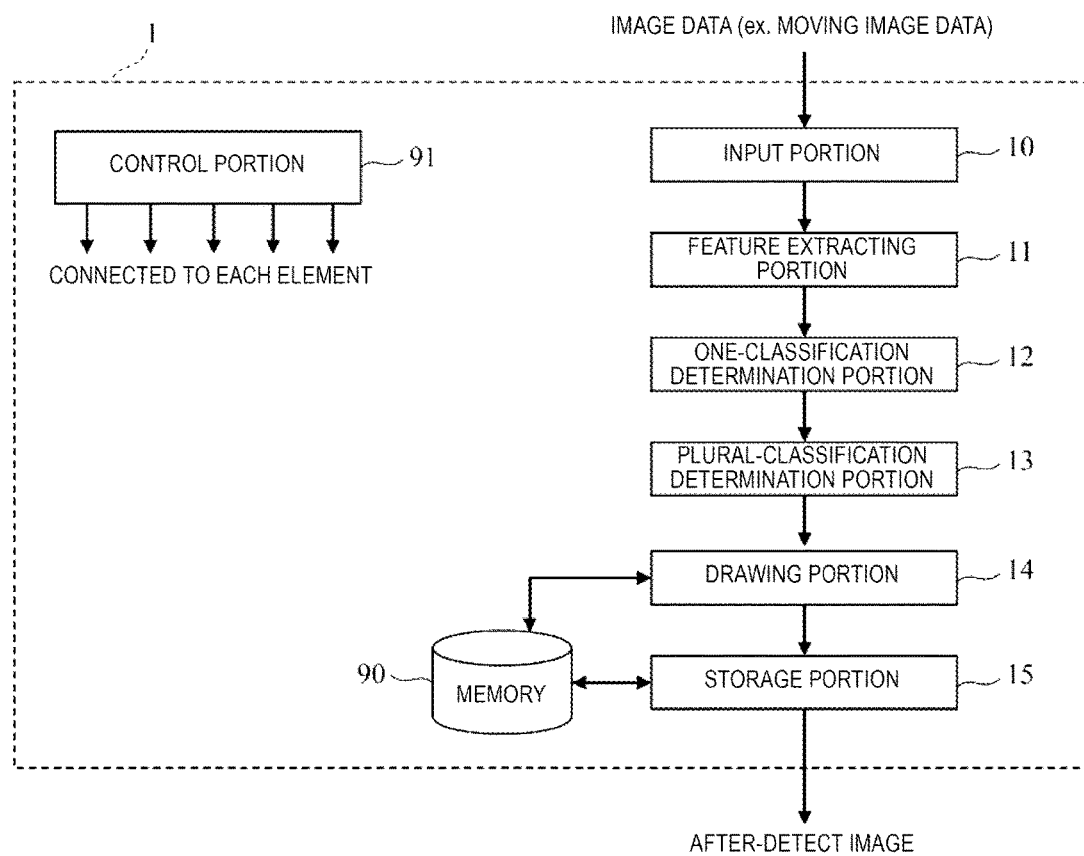

[Fig. 2]
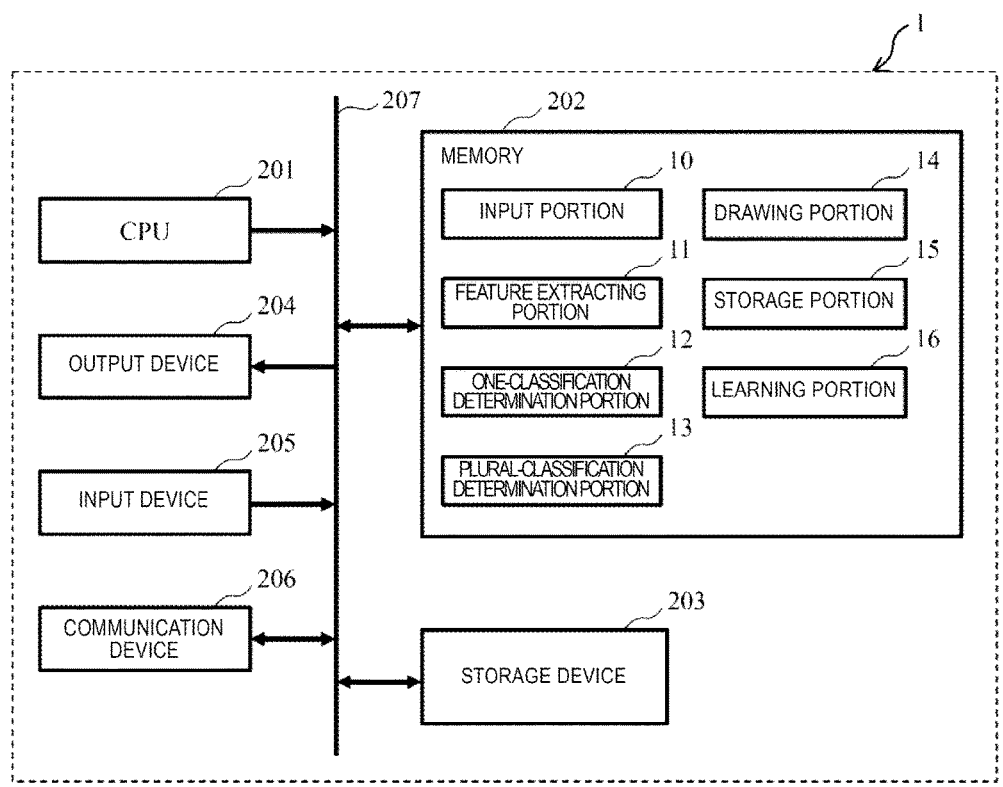

[Fig. 3]
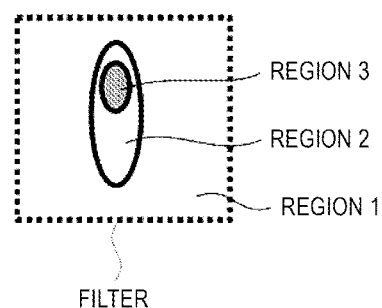
FILTER
[Fig. 4]
FILTER
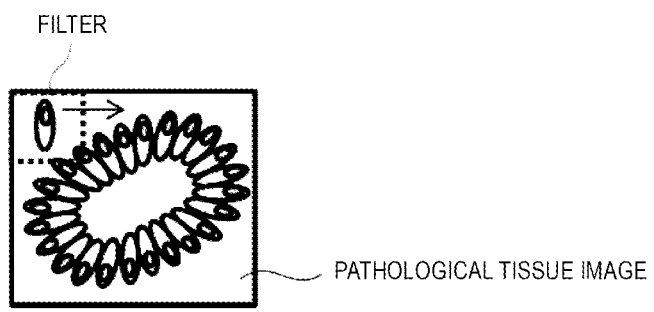
PATHOLOGICAL TISSUE IMAGE

[Fig. 5]
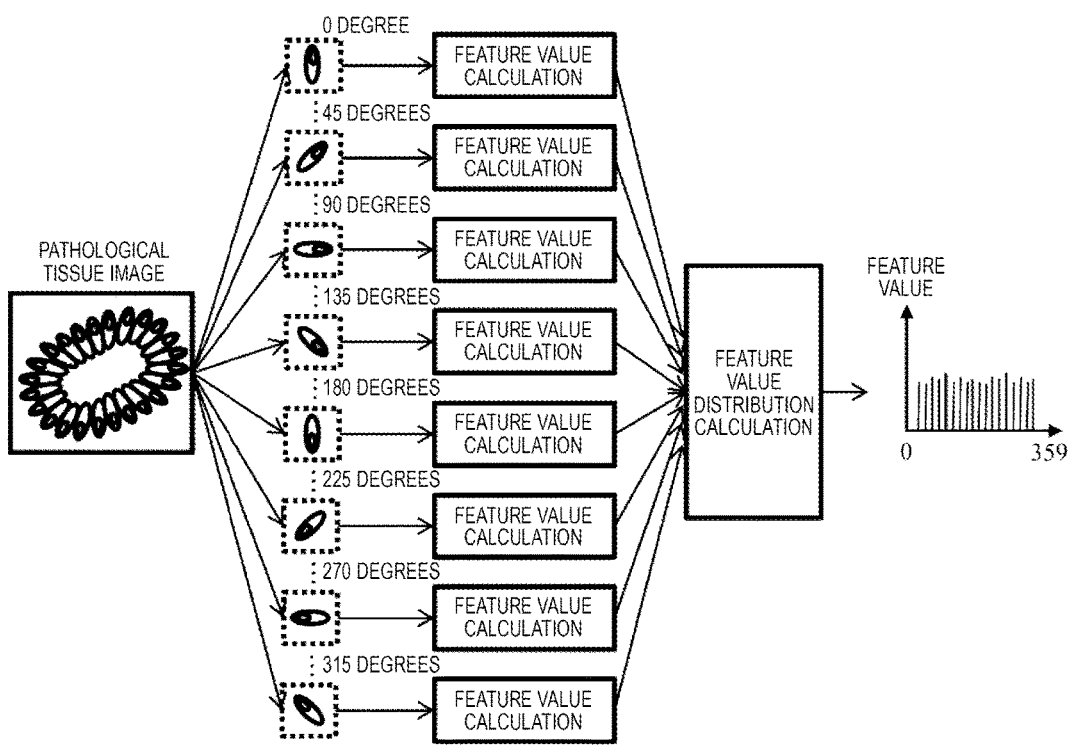

[Fig. 6]
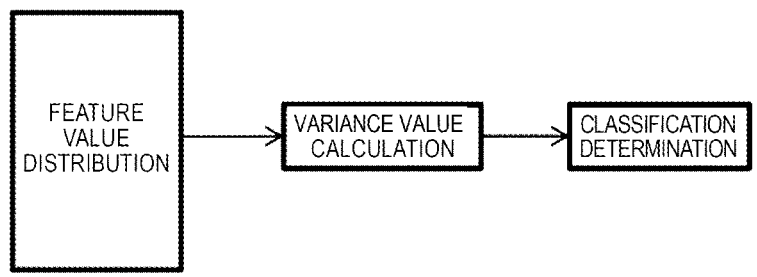
(a)
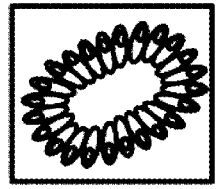
(b)
① NORMAL CELLS (UNIFORM SHAPE)
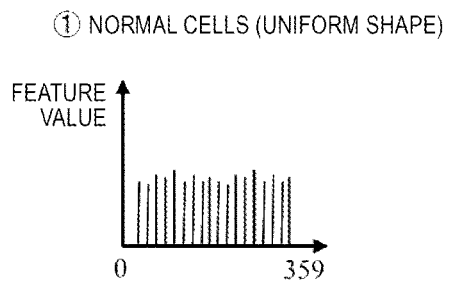
(c)
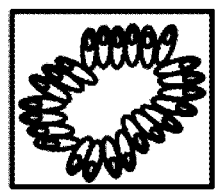
(d)
② ABNORMAL CELLS (UNUNIFORM SHAPE)
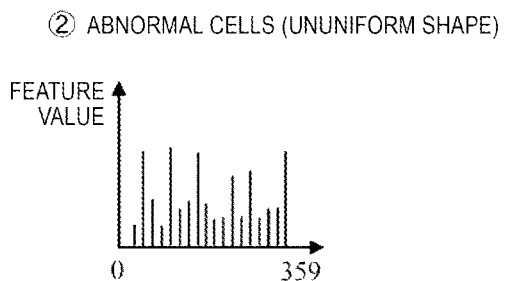

[Fig. 7]

| • CANCER DETERMINATION | NORMAL | CANCER | CANCER PROBABILITY | DISPLAY |
|---|---|---|---|---|
| ▦ POORLY DIFFERENTIATED TUBULAR ADENOCARCINOMA | ○ | ● | 0.89 | IMAGE |
| ▦ MODERATELY DIFFERENTIATED TUBULAR ADENOCARCINOMA | ● | ○ | 0.31 | IMAGE |
| ▦ WELL DIFFERENTIATED TUBULAR ADENOCARCINOMA | ● | ○ | 0.21 | IMAGE |
| ▦ PAPILLARY ADENOCARCINOMA | ● | ○ | 0.11 | IMAGE |
| ▦ SIGNET-RING CELL CARCINOMA | ● | ○ | 0.05 | IMAGE |

CANCER PROBABILITY DETERMINATION RESULT: POORLY DIFFERENTIATED TUBULAR ADENOCARCINOMA

[Fig. 8]

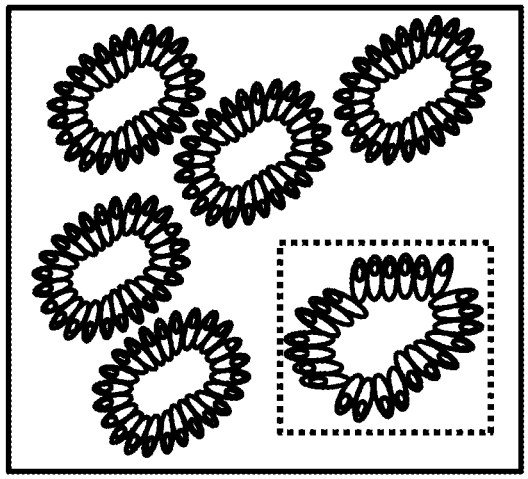

[Fig. 9]
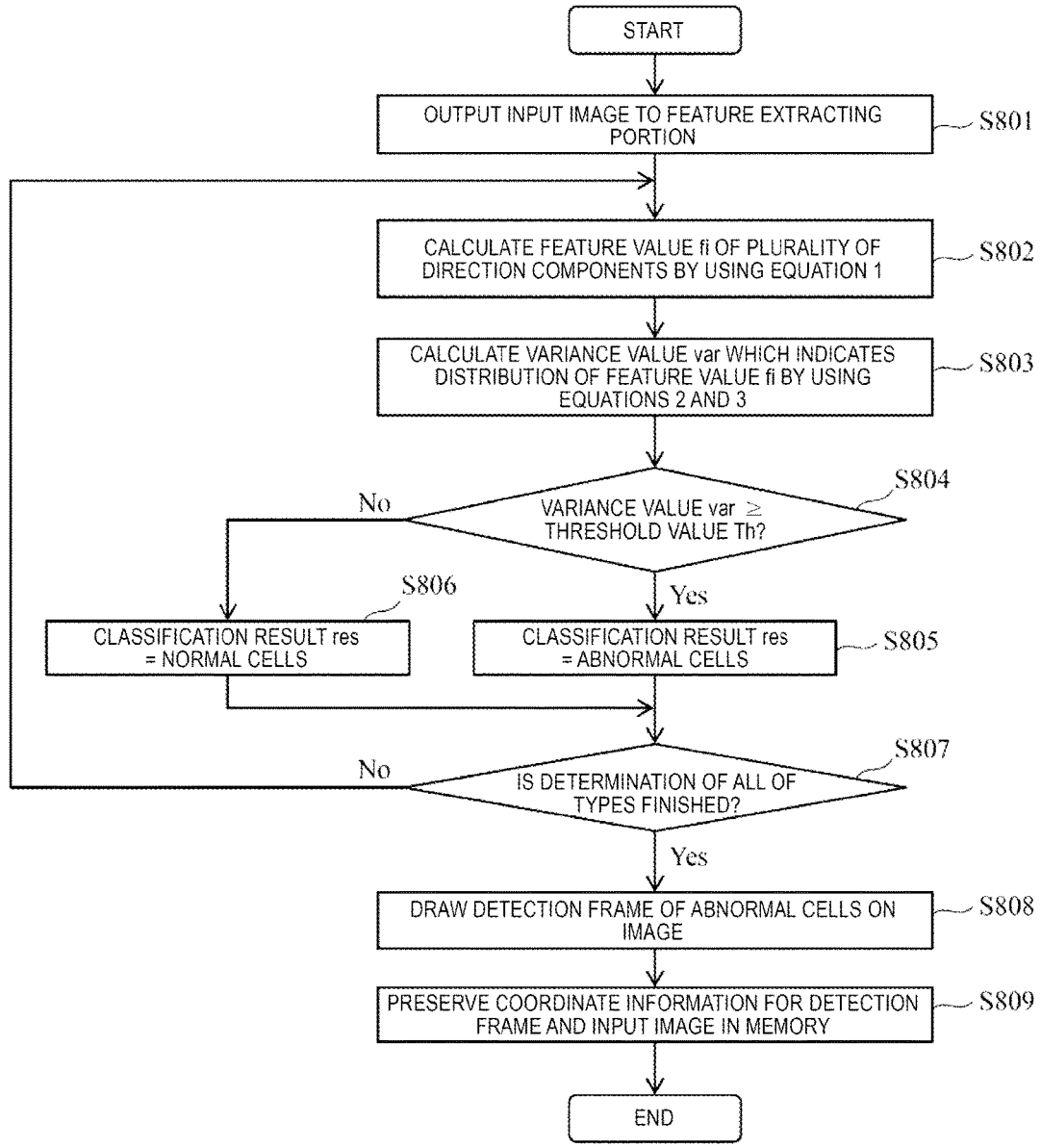

[Fig. 10]
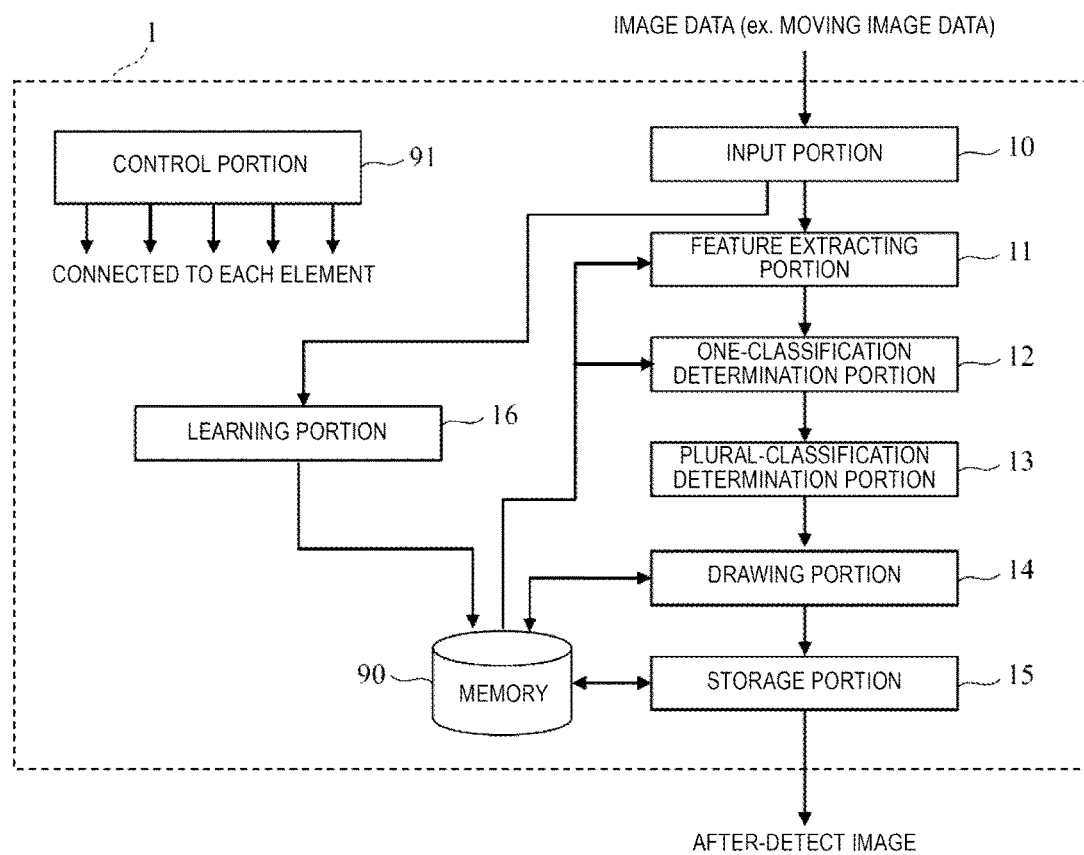

[Fig. 11]
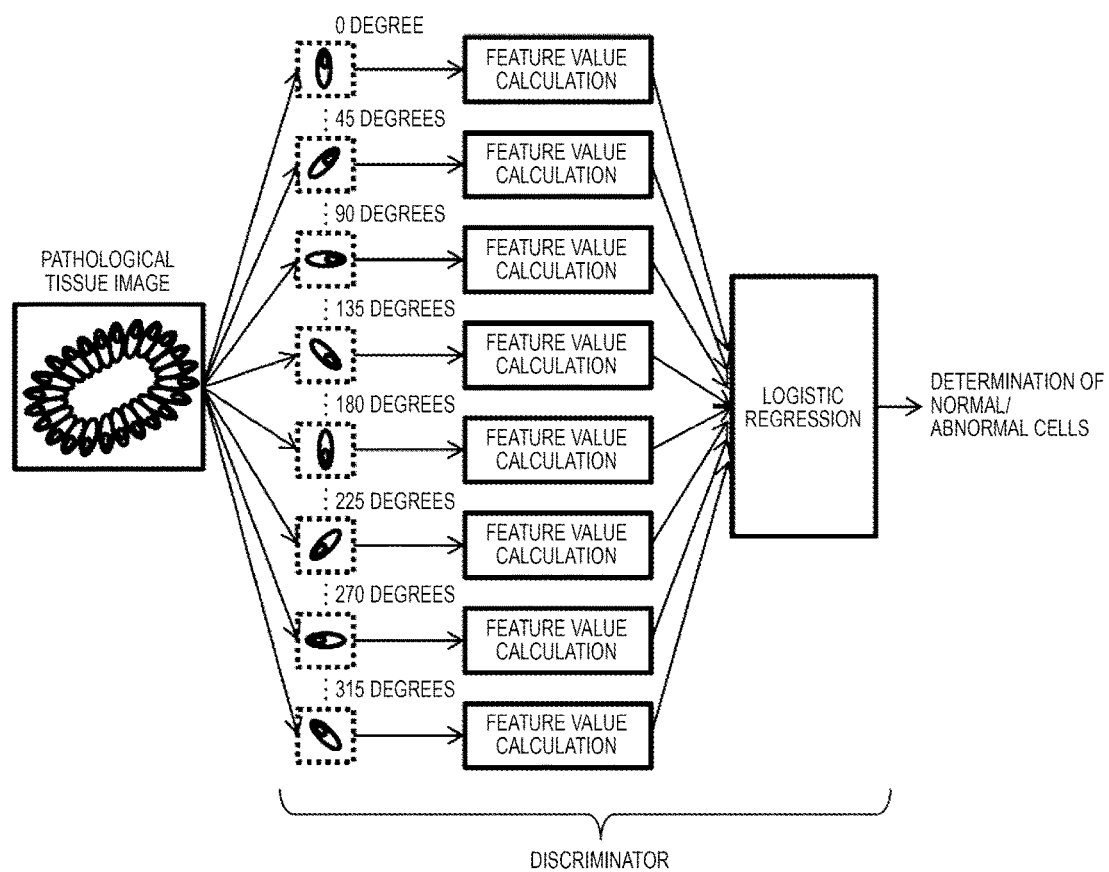

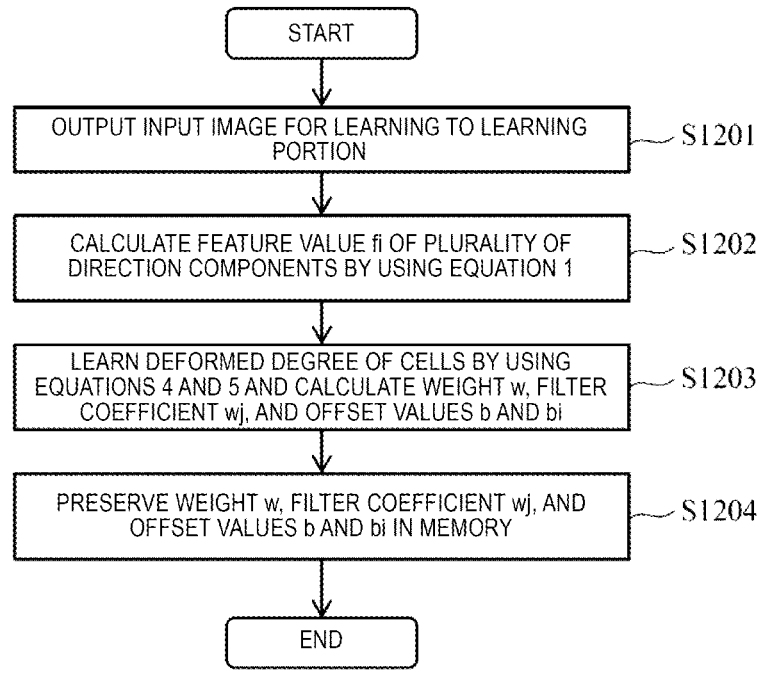
[Fig. 12]

[Fig. 13]
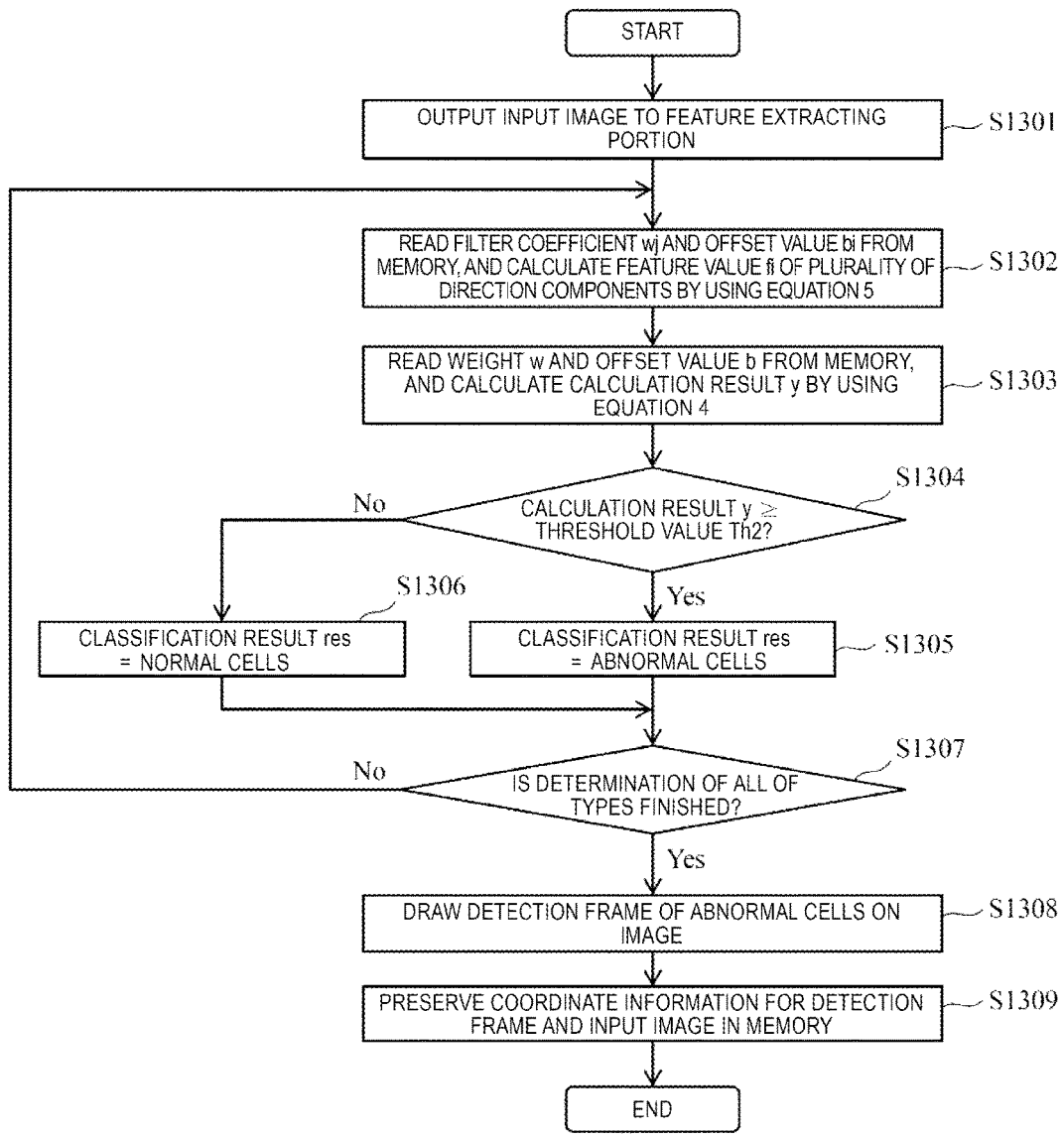

[Fig. 14]
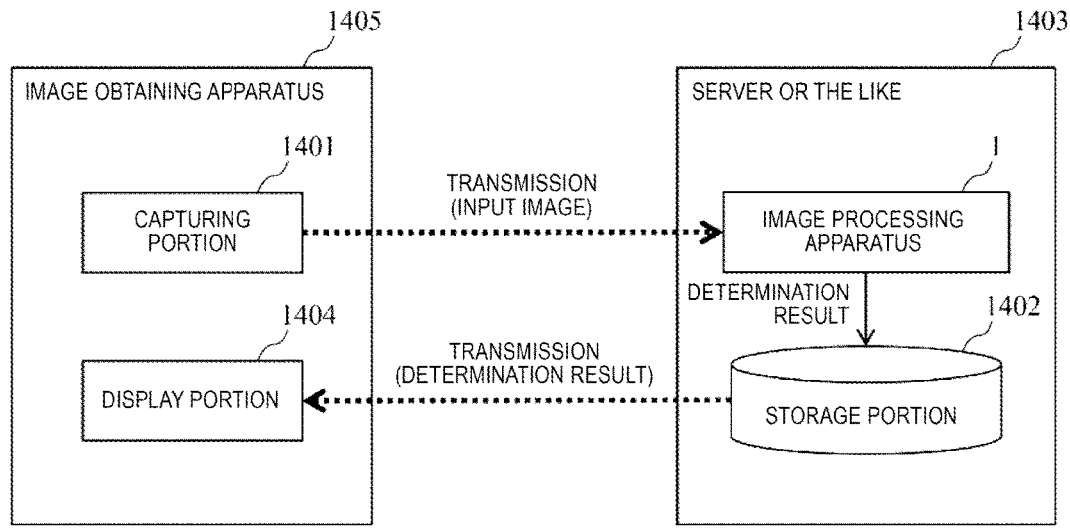
1400
[Fig. 15]
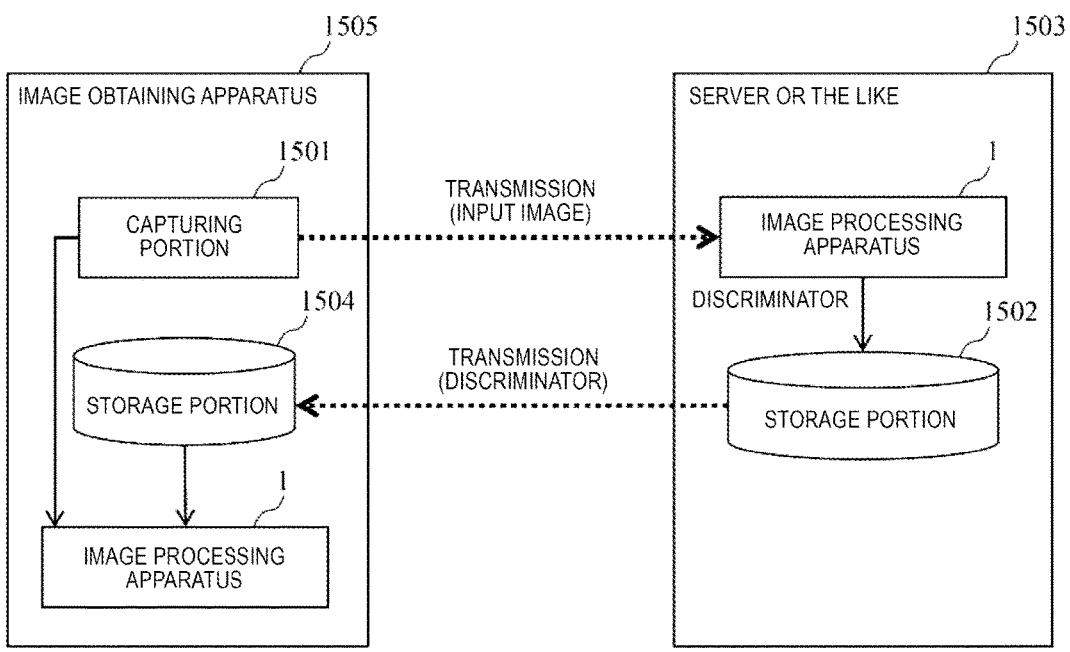
1500

CYTOLOGIC DIAGNOSIS SUPPORT APPARATUS, CYTOLOGIC DIAGNOSIS SUPPORT METHOD, REMOTE DIAGNOSIS SUPPORT SYSTEM, SERVICE PROVIDING SYSTEM, AND IMAGE PROCESSING METHOD

TECHNICAL FIELD

The present invention relates to a cytologic diagnosis support apparatus, a cytologic diagnosis support method, a remote diagnosis support system, a service providing system, and an image processing method, and for example, to an image processing technology for supporting the cytologic diagnosis.

BACKGROUND ART

In recent years, in the diagnosis of illness, "pathological diagnosis" using microscopic observation of tissue preparation of a lesioned part occupies a significant position. In the pathological diagnosis, the process from specimen preparation to diagnosis requires a lot of manpower, and automation is difficult. In particular, ability and experiment of a pathologist are important in diagnosis, and the diagnosis depends on personal ability of the pathologist. Meanwhile, the number of cancer patients increases due to population aging, and the number of pathologists is not sufficient at a medical site. From above, needs for image processing technology or remote diagnosis which supports the pathological diagnosis is increasing. In this manner, in order to classify a pathological tissue for supporting the pathological diagnosis, for example, there is a technology suggested in PTL 1. In PTL 1, low-magnification images are generated from high-magnification images, images are simply classified by the low-magnification images, and then, pathological tissues are classified by using the high-magnification images which are a base of the low-magnification images.

CITATION LIST

Patent Literature

PTL 1: JP-A-2010-203949

SUMMARY OF INVENTION

Technical Problem

However, in tissue and cell images, there is a case where the tissues and cells have various shapes in accordance with the type of abnormal cells (for example, cancer) or a degree of progress of abnormal cells (for example, cancer), and there is a case where the abnormal cells correspond to a plurality of suspicious classifications in accordance with the degree of progress of abnormal cells (for example, cancer). Therefore, there is a problem that there is a possibility of misdiagnosis when narrowing the classifications down to one classification. Therefore, as described in PTL 1, in a case of classifying the tissues and cells by using the high-magnification images which are a base of the low-magnification images after generating the low-magnification images from the high-magnification images and simply classifying the images by the low-magnification images, even when there is a possibility that the cells correspond to the plurality of types of abnormal cells, the cells are narrowed down to one classification, and misdiagnosis is caused.

In addition, there are needs for classifying the tissues and cells from one image in the pathological diagnosis. However, in PTL 1, it is necessary to use both of the high-magnification and low-magnification images, and there is a problem that the tissues and cells cannot be classified from one image.

Considering the situation, the present invention provides a technology for realizing determination of tissues and cells from one image even in a case where the tissues or cells have various shapes due to type of abnormal cells (for example, cancer) or the degree of progress of abnormal cells (for example, cancer).

Solution to Problem

In order to solve the problem, in the present invention, feature values of a deformation degree of cells are calculated for each type of abnormal cells (for example, cancer). More specifically, a cytologic diagnosis support apparatus according to the present invention executes processing of extracting feature values of a plurality of direction components from a target image, processing of determining whether or not the image corresponds to one classification by using the plurality of feature values, and processing of determining whether or not the determination processing is finished with respect to all of the classifications set in advance.

More features related to the present invention will be apparent from the description and the attached drawings of the specification. In addition, aspects of the present invention are achieved and realized by elements, combination of the various elements, the following detailed description, and the aspects of the range of the attached claims.

The description of the specification is merely a typical example, and it is necessary to understand that the description does not limit the range of the claims of the present invention or application examples to any meaning.

Advantageous Effects of Invention

According to the present invention, even in a case where tissues or cells have different shapes in accordance with the type of abnormal cells (for example, cancer) or the degree of progress of abnormal cells (for example, cancer), by calculating the feature values of the deformed degree of the cells for each type of the abnormal cells (for example, cancer), it is possible to suppress misdetection or over-detection, and to classify the tissues and cells from one image.

BRIEF DESCRIPTION OF DRAWINGS

FIG. 1 is a block diagram illustrating a function of an image processing apparatus according to a first embodiment of the present invention.

FIG. 2 is a view illustrating a hardware configuration example of the image processing apparatus according to the first and second embodiments of the present invention.

FIG. 3 is a view for describing an example of a filter of a feature extracting portion 11.

FIG. 4 is a view for describing an example of an operation in one direction of the feature extracting portion 11.

FIG. 5 is a view for describing an example of operations in a plurality of directions of the feature extracting portion 11 according to the first embodiment.

FIG. 6 is a view for describing an example of an operation of a one-classification determination portion 12.

FIG. 7 is a view for describing an example of a GUI of cancer determination.

FIG. 8 is a view for describing an example of an operation of a drawing portion 14.

FIG. 9 is a flowchart for describing the entire operation of an image processing apparatus 1 according to the first embodiment.

FIG. 10 is a block diagram illustrating a function of the image processing apparatus according to the second embodiment of the present invention.

FIG. 11 is a view for describing an example of an operation of the one-classification determination portion 12 according to the second embodiment.

FIG. 12 is a flowchart for describing an operation of a learning portion 16.

FIG. 13 is a flowchart for describing the entire operation of the image processing apparatus 1 according to the second embodiment.

FIG. 14 is a view illustrating a schematic configuration of a remote diagnosis support system in which the image processing apparatus of the present invention is loaded.

FIG. 15 is a view illustrating a schematic configuration of a net entrusting service providing system in which the image processing apparatus of the present invention is loaded.

DESCRIPTION OF EMBODIMENTS

The present invention relates to an image processing technology for detecting specific tissues and cells (for example, cancer) included in an image obtained by capturing a slice of the tissues and cells on a slide glass by a capturing device, such as a camera having a microscope loaded thereon. The embodiments of the present invention provide an image processing apparatus and an image processing method which realize suppression of false negative and misdetection of abnormal cells (for example, cancer) by capturing a deformed degree of the cells, by calculating probability of abnormal cells (for example, cancer) by determining the presence or absence of the abnormal cells (for example, cancer) for each type of the abnormal cells (for example, cancer), and further by classifying the abnormal cells (for example, cancer) from the determination result of all of the types set in advance.

Hereinafter, the embodiments of the present invention will be described with reference to the attached drawings. In the attached drawings, there is also a case where the same functional elements are indicated by the same numbers. In addition, the attached drawings illustrate specific embodiments and implementation examples in accordance with a principle of the present invention, but the drawings are for understanding the present invention, and are not used for limiting the interpretation of the present invention by no means.

In the embodiments, description of the embodiments is sufficiently detailed for those skilled in the art to realize the present invention, but other implementation and aspects are also possible, and it is necessary to understand that changes of configurations and manufacturing or replacement of various elements are possible without departing from the range and spirit of the technical idea of the present invention. Therefore, the following description should not be interpreted being limited thereto.

Furthermore, as will be described later, the embodiments of the present invention may be implemented by software that is operated on a general-purpose computer, or may be implemented by dedicated hardware or by a combination of the software and the hardware.

Hereinafter, each processing will be described in the embodiments of the present invention considering "each processing portion (for example, feature extracting portion or the like) which functions as a program" as a subject (operation subject), but determined processing is performed while using a memory and a communication port (communication control device) by executing the program by a processor (CPU or the like), and thus, the processor may be described as a subject.

(1) First Embodiment

<Functional Configuration of Image Processing Apparatus>

FIG. 1 is a block diagram illustrating a functional configuration of an image processing apparatus according to the embodiment of the present invention. An image processing apparatus 1 includes an input portion 10, a feature extracting portion 11, a one-classification determination portion 12, a plural-classification determination portion 13, a drawing portion 14, a storage portion 15, a control portion 91, and a memory 90. The image processing apparatus may be mounted in a tissues and cells image obtaining apparatus, such as a virtual slide, and as will be described later (third and fourth embodiments), may be mounted in a server connected to the tissues and cells image obtaining apparatus via a network.

In the image processing apparatus 1, the input portion 10, the feature extracting portion 11, the one-classification determination portion 12, the plural-classification determination portion 13, the drawing portion 14, and the storage portion 15 may be realized by a program, or may be realized by being made in modules.

Image data is input into the input portion 10. For example, the input portion 10 may obtain still image data or the like which is captured at a predetermined time interval by capturing means, such as camera built in a microscope, and is encoded in JPG, Jpeg2000, PNG, or BMP format, and may set the image as an input image. In addition, the input portion 10 may extract the still image data of frames at a predetermined interval from moving image data, such as MotionJPEG, MPEG, H.264, or HD/SDI format, and may set the image as an input image. In addition, the input portion 10 may set the image obtained by the capturing means via a bus or the network as an input image. In addition, the input portion 10 may set the image stored in advance in an attachable and detachable storage medium as an input image.

The feature extracting portion 11 extracts feature values of a plurality of direction components related to the cells from the image.

The one-classification determination portion 12 calculates the deformed degree of the cells from the extracted feature values, and classifies the cells into normal cells or abnormal cells regarding the one-classification.

The plural-classification determination portion 13 classifies the tissues and cells by using the classification result of the plurality of one-classifications set in advance.

The drawing portion 14 draws a detection frame on the image to surround abnormal cells classified by the plural-classification determination portion 13.

The storage portion 15 preserves the image obtained by drawing the detection frame on an original image by the drawing portion 14, in the memory 90.

The control portion 91 is realized by the processor, and is connected to each of the elements in the image processing apparatus 1. Operations of each of the elements of the image processing apparatus 1 are operations performed by an autonomous operation of each of the above-described configuration elements or an indication of the control portion 91.

In this manner, in the image processing apparatus 1 of the embodiment, by using the feature value that indicates the deformed degree of the cells acquired by the feature extracting portion 11, the cells are classified into normal cells or abnormal cells regarding the one-classification by the one-classification determination portion 12, and the tissues and cells are classified by using the classification result of the plurality of one-classifications set in advance by the plural-classification determination portion 13.

<Hardware Configuration of Image Processing Apparatus>

FIG. 2 is a view illustrating a hardware configuration example of the image processing apparatus 1 according to the embodiment of the present invention.

The image processing apparatus 1 includes a CPU (processor) 201 which executes various programs, a memory 202 which stores various programs therein, a storage device (corresponds to the memory 90) 203 which stores various data therein, an output device 204 for outputting an after-detection image, an input device 205 for inputting instruction, an image or the like by a user, and a communication device 206 for performing communication with other devices, and the members are connected to each other by a bus 207.

The CPU 201 reads various programs from the memory 202 as necessary, and executes the programs.

The memory 202 stores the input portion 10, the feature extracting portion 11, the one-classification determination portion 12, the plural-classification determination portion 13, the drawing portion 14, and the storage portion 15 therein as programs. In addition, the learning portion 16 is a necessary configuration in the second embodiment, and the image processing apparatus 1 according to the first embodiment does not include the learning portion 16.

The storage device 203 stores a processing target image, the classification result of one-classification generated by the one-classification determination portion 12 and the numerical value thereof, the classification result of the tissues and cells generated by the plural-classification determination portion 13, and positional information or the like for drawing the detection frame generated by the drawing portion 14.

The output device 204 is configured of devices, such as a display, a printer, or a speaker. For example, the output device 204 displays the data generated by the drawing portion 14 on a display screen.

The input device 205 is configured of devices, such as a keyboard, a mouse, and a microphone. The instruction (including determination of the processing target image) by the user is input to the image processing apparatus 1 by the input device 205.

The communication device 206 is not a necessary configuration in the image processing apparatus 1, and in a case where the communication device is included in a personal computer or the like connected to the tissues and cells image obtaining apparatus, the image processing apparatus 1 may not hold the communication device 206. The communication device 206 receives the data (including the image) sent from other devices (for example, server) connected, for example, via a network, and performs an operation of storing the data in the storage device 203.

<Configurations and Operations of Each Portion>

Hereinafter, configurations and operations of each element will be described in detail.

(i) Feature Extracting Portion 11

The feature values of the plurality of direction components are acquired. As an example, a filter which acquires the feature values in a direction of 0 degree is illustrated in FIG. 3. For example, filter coefficients of a region 1 (region other than the cells and cell nuclei), a region 2 (region of cells), and a region 3 (region of cell nuclei) in FIG. 3 are respectively set to be 0, 1, and −1. As illustrated in FIG. 4, by using Equation 1, the calculation results of each of the filters are acquired from an upper left side to a lower right side of the target image, and by dividing the sum of the calculation result by the number of processing N, a feature value fi of the filter at 0 degree (i=0) is acquired. However, in Equation 1, pj indicates a pixel value, kj indicates a filter coefficient, and m indicates the number of filter coefficients. Similarly, as illustrated in FIG. 5, by using the filter which acquires the feature value in the direction from 0 degree to 359 degrees, the feature values of each direction will be calculated. Next, as illustrated in FIG. 5, by using each of the feature values (f0 to f359) from 0 degree to 359 degrees, distribution of the feature values is calculated. However, in FIG. 5, the filter which acquires the feature values in each direction is used, but by using the filter which acquires the feature value in one direction and images obtained by rotating the target image by one degree at a time, the feature values fi in each direction may be acquired.

$$fi = \Sigma_{r=1}^{N} \Sigma_{j=1}^{m} (pj \times kj)/N \quad \text{Equation 1}$$

(ii) One-Classification Determination Portion 12

As illustrated in FIG. 6, the one-classification determination portion 12 calculates a variance value var of distribution of the feature values fi by using Equations 2 and 3 from the distribution of the feature value fi acquired by the feature extracting portion 11. In Equation 2, fav indicates an average value of fi, and fsd indicates a standard deviation of fi. In addition, in Equation 3, t indicates the number of plurality of direction components to be acquired, for example, 360.

$$zi = (fi - fav)/fsd \quad \text{Equation 2}$$

$$var = \Sigma_{i=1}^{t} zi^2 / t \quad \text{Equation 3}$$

Next, the calculated variance value var shows uniformity of the cells, and classifies the cells into normal cells or abnormal cells from the variance value. The calculated variance value is a value of probability of abnormal cells (for example, cancer). As illustrated in FIG. 6(a), in a case where the images of the tissues and cells including the cells having a uniform shape are input, a feature value distribution illustrated in FIG. 6(b) is achieved, the variance value var which indicates the value of probability of abnormal cells (for example, cancer) becomes less than a threshold value Th, and thus, the input target image is classified as normal cells. Meanwhile, as illustrated in FIG. 6(c), in a case where the images of the tissues and cells including the cells having ununiform shape are input, the feature value distribution illustrated in FIG. 6(d) is achieved, the variance value var which indicates the value of probability of abnormal cells (for example, cancer) becomes equal to or greater than a threshold value Th, and thus, the input target image is classified as abnormal cells.

FIG. 7 is a view illustrating an example of a graphical user interface (GUI) of cancer determination as one example of the cell determination. FIG. 7 is one example of a case of a stomach cancer, and is a view illustrating the classification result of poorly differentiated tubular adenocarcinoma, moderately differentiated tubular adenocarcinoma, well differentiated tubular adenocarcinoma, papillary adenocarcinoma, and signet-ring cell carcinoma. In the example of FIG. 7, an example in which the one-classification determination portion 12 classifies that the poorly differentiated tubular adenocarcinoma which is abnormal cells is included in the input target image, and calculates the value of cancer probability of the poorly differentiated tubular adenocarcinoma as 0.89, with respect to the poorly differentiated tubular adenocarcinoma. In addition, an example in which the one-classification determination portion 12 classifies that the moderately differentiated adenocarcinoma which is abnormal cells is not included in the input target image and the cells are normal cells, and calculates the value of identify of the moderately differentiated adenocarcinoma as 0.31, with respect to the moderately differentiated adenocarcinoma, is illustrated. In addition, an example in which the one-classification determination portion 12 classifies that the well differentiated tubular adenocarcinoma which is abnormal cells is not included in the input target image and the cells are normal cells, and calculates the value of the cancer probability of the well differentiated tubular adenocarcinoma as 0.21, with respect to the well differentiated tubular adenocarcinoma, is illustrated. In addition, an example in which the one-classification determination portion 12 classifies that the papillary adenocarcinoma which is abnormal cells is not included in the input target image and the cells are normal cells, and calculates the value of the cancer probability of the papillary adenocarcinoma as 0.11, with respect to the papillary adenocarcinoma, is illustrated. In addition, an example in which the one-classification determination portion 12 classifies that the signet-ring cell carcinoma which is abnormal cells is not included in the input target image and the cells are normal cells, and calculates the value of the cancer probability of the papillary adenocarcinoma as 0.05, with respect to the papillary adenocarcinoma, is illustrated.

(iii) Plural-Classification Determination Portion 13

The plural-classification determination portion 13 displays only the type of the abnormal cells (for example, cancer) which exceeds the threshold value Th in the determination result of the probability of abnormal cells (for example, cancer) by comparing the value of the probability of abnormal cells (for example, cancer) which is the result of the plurality of one-classifications that are acquired by the one-classification determination portion 12 and set in advance, and the arbitrary threshold value Th with each other. In the example of FIG. 7, the poorly differentiated tubular adenocarcinoma is displayed in the cancer probability determination result. According to the degree of progress or the type of the abnormal cells (for example, cancer), there is a case where the type is determined as the type of the plurality of abnormal cells (for example, cancer). Therefore, there is also a case where the value of the probability of the plurality of abnormal cells (for example, cancer) exceeds the threshold value Th, and in this case, the type of the plurality of abnormal cells (for example, cancer) is displayed in the determination result of the probability of abnormal cells (for example, cancer).

(iv) Drawing Portion 14

In the one-classification determination portion 12, with respect to items determined as the abnormal cells (for example, cancer), in FIG. 7, in a case of pressing an "image" button, as illustrated in FIG. 8, the drawing portion 14 draws the detection frame in the input target image for indicating locations of suspicious abnormal cells (for example, cancer). Meanwhile, with respect to the items determined as the normal cells, in FIG. 7, in a case of pressing the "image" button, the detection frame is not drawn on the input target image, and the input target image is displayed as it is.

(v) Storage Portion 15

The storage portion 15 preserves coordinate information for drawing the detection frame on the input target image by the drawing portion 14 and the target image in the memory 90.

<Processing Order of Image Processing Apparatus>

FIG. 9 is a flowchart for describing an operation of the image processing apparatus 1 according to the embodiment of the present invention. Hereinafter, each processing portion (the input portion 10, the feature extracting portion 11, or the like) will be described as operation subjects, but the CPU 201 may be an operation subject, and the CPU 201 may be loaded such that each of the processing portions which function as the programs is executed.

(i) Step 801

The input portion 10 receives the input image and outputs the input image to the feature extracting portion 11.

(ii) Step 802

The feature extracting portion 11 acquires the feature values fi of the plurality of direction components by using the above-described Equation 1.

(iii) Step 803

The one-classification determination portion 12 calculates the variance value var which indicates the distribution of the feature value fi by the above-described Equations 2 and 3 by using the feature value fi output by the feature extracting portion 11.

(iv) Step 804

The one-classification determination portion 12 compares the calculated variance value var and the threshold value Th. In other words, in a case of variance value var≥threshold value Th, the processing moves to step 805. Meanwhile, in a case of var<threshold value Th, the processing moves to step 806.

(v) Step 805

The one-classification determination portion 12 sets the abnormal cells (for example, 1) in a classification result res.

(vi) Step 806

The one-classification determination portion 12 sets the normal cells (for example, 0) in the classification result res.

(vii) Step 807

The plural-classification determination portion 13 repeats the processing from the above-described steps 802 to 806 in order to perform the one-classification determination portion 12 with respect to all of the types set in advance. By repeating steps 802 to 806, it is possible to determine whether the cells are normal cells or abnormal cells with respect to all of the types set in advance. In addition, since the coefficients of the filter (FIG. 3) for acquiring the feature value fi with respect to each of the types are different from each other, the filter coefficient is changed in a case of performing the classification processing with respect to another type, and the processing moves to step 802. When it is determined that the determination of all of the types is finished, the processing moves to step 808.

(viii) Step 808

The drawing portion 14 draws the detection frame which indicates abnormal cells on the image and displays the detection frame when pressing the image button illustrated in FIG. 7, with respect to the type determined as abnormal cells. The drawing portion 14 does not draw the detection frame on the image when pressing the image button illustrated in FIG. 7 with respect to the type determined to be normal cells.

(ix) Step 809

The storage portion 15 preserves the coordinate information for drawing the detection frame on the input target image by the drawing portion 14 and the target image in the memory 90 (corresponds to the storage device 203).

According to the embodiment of the present invention, by using the feature values of the plurality of direction components, the distribution value which indicates the deformed degree of the cells is acquired. Therefore, regarding the one-classification, it is possible to suppress misdetection or over-detection, and to classify the cells into normal cells or abnormal cells from one image.

In addition, by using the classification result of the plurality of one-classifications set in advance, in order to classify the tissues and cells, it is possible to perform determination of the probability of abnormal cells (for example, cancer) which corresponds to the degree of progress of abnormal cells (for example, cancer).

In addition, not by determining all of the classifications at once, but by determining whether or not the type corresponds to each of the classifications, it is possible to perform determination that the misdetection is suppressed.

(2) Second Embodiment

The image processing apparatus 1 according to the second embodiment will be described in FIG. 10. As illustrated in FIG. 10, configurations which are the same as those of FIG. 1 of the first embodiment are included, but the operations of the feature extracting portion 11 and the one-classification determination portion 12 are different from those of FIG. 1. In addition, the learning portion 16 is added. Therefore, here, configurations having different processing and additional configurations will be described by using FIG. 10, and the entire processing flow different from that of FIG. 9 will be described by using FIG. 13.

<Configuration's and Operations of Each Portion>

Hereinafter, configurations and operations of each element different from those of FIG. 1 will be described in detail.

(i) Learning Portion 16

The learning portion 16 includes the same configuration as that of the feature extracting portion 11 and the one-classification determination portion 12 on the inside thereof, and by using this, for example, by using a technology of machine learning which is the technology of the related art, the learning portion 16 learns the deformed degree of the cells. In addition, an input image to be learned by the learning portion 16 and images input as an image as an evaluation target are different from each other.

In other words, in the feature values fi of the plurality of direction components acquired by the feature extracting portion 11, the information which indicates the shape of a part of the cells is included.

As illustrated in FIG. 11, by using the feature values fi of the plurality of direction components acquired by the feature extracting portion 11, when the cells in the input image of tissues and cells are the normal cells according to Equations 4 and 5, for example, by logistic regressive processing, in order to determine that the cells are normal cells, the one-classification determination portion 12 learns the deformed degree of the cells, for example, by using the technology of the machine learning which is the technology of the related art. In addition, when the cells in the input images of the tissues and cells are abnormal cells, by the logistic regressive processing, in order to determine that the cells are abnormal cells, the one-classification determination portion 12 learns the deformed degree of the cells. However, in Equation 4, w indicates a weight matrix, f is a matrix of each of the direction components fi acquired from the input image, b indicates an offset value, g indicates a nonlinear function, and y indicates the calculation result, respectively, and the weight w and the offset value b are acquired by the machine learning. In addition, in Equation 5, pj indicates a pixel value, wj indicates a filter coefficient, bi indicates an offset value, m indicates the number of filter coefficients, N indicates the number of processing, and h indicates a nonlinear function. For example, as the technology of machine learning, Convolutional Neural Network may be used.

$$y = g(w \times f + b) \qquad \text{Equation 4}$$

$$fi = \Sigma_{r=1}^{N} h(\Sigma_{j=1}^{m}(pj \times wj) + bi)/N \qquad \text{Equation 5}$$

By using the plurality of images for learning, the learning portion 16 repeatedly executes the feature extracting portion 11 and the one-classification determination portion 12, acquires the weight w, the filter coefficient wj, and the offset values b and bi, and creates the discriminator which determines whether or not the cells are normal cells or abnormal cells. In addition, the learning portion 16 stores the acquired weight w, the filter coefficient wj, and the offset values b and bi in the memory.

(ii) Feature Extracting Portion 11

The feature extracting portion 11 reads the filter coefficient wj and the offset value bi from the memory, and calculates the feature value fi of each direction by using the filter which acquires the feature values in the directions from 0 degree to 359 degrees as illustrated in FIG. 11 by using Equation 5 with respect to the input image determined to be output from the input portion 10.

(iii) One-Classification Determination Portion 12

The one-classification determination portion 12 reads the weight w and the offset value b from the memory, and determines whether or not the cells are normal cells or abnormal cells from the feature value fi acquired by the feature extracting portion 11 as illustrated in FIG. 11 by using Equation 5.

<Hardware Configuration of Image Processing Apparatus>

The hardware configuration example of the image processing apparatus 1 according to the embodiment of the present invention is similar to that of FIG. 2. However, in a case of the second embodiment, the image processing apparatus 1 is different from that of the first embodiment, and stores the learning portion 16 in the memory 202. Except for this, the hardware configuration of the image processing apparatus 1 is the same as that of the image processing apparatus 1.

<Processing Order of Image Processing Apparatus>

FIG. 12 is a flowchart for describing an operation of the learning portion 16 of the image processing apparatus 1 according to the embodiment of the present invention. Hereinafter, the learning portion 16 will be described as the operation subject, but the CPU 201 may be considered as an operation subject, and may be loaded such that the CPU 201 executes each of the processing portions which function as the programs.

(i) Step 1201

The input portion 10 receives the image input for learning, and outputs the input image to the learning portion 16.

(ii) Step 1202

The learning portion 16 acquires the feature values fi of the plurality of direction components by using the above-described Equation 1.

(iii) Step 1203

The learning portion 16 learns the deformed degree of the cells by using Equations 4 and 5, and calculates the weight w, the filter coefficient wj, and the offsets b and bi.

(iv) Step 1204

The learning portion 16 preserves the calculated weight w, the filter coefficient wj, and the offsets b and bi in the memory 90. In addition, the weight w, the filter coefficient wj, and the offsets b and bi are acquired with respect to all of the types (for example, all types of cancer cells) set in advance by the learning.

FIG. 13 is a flowchart for describing the operation of the image processing apparatus 1 according to the embodiment of the present invention. Hereinafter, each of the processing portions (the input portion 10, the feature extracting portion 11, or the like) will be described as the operation subject, but the CPU 201 may be considered as an operation subject, and may be loaded such that the CPU 201 executes each of the processing portions which function as the programs.

(i) Step 1301

The input portion 10 receives the input image to be determined and outputs the input image to the feature extracting portion 11.

(ii) Step 1302

The feature extracting portion 11 reads the filter coefficient wj and the offset bi from the memory 90, and acquires the feature values fi of the plurality of direction components by using the above-described Equation 5.

(iii) Step 1303

The one-classification determination portion 12 reads the weight w and the offset b from the memory 90, and calculates a calculation result y by the Equation 4.

(iv) Step 1304

The one-classification determination portion 12 compares the calculated calculation result y and a threshold value Th2. In other words, in a case of calculation result y≥threshold value Th2, the processing moves to step 1305. Meanwhile, in a case of calculation result y<threshold value Th2, the processing moves to step 1306.

(v) Step 1305

The one-classification determination portion 12 sets the abnormal cells (for example, 1) in the classification result res.

(vi) Step 1306

The one-classification determination portion 12 sets the normal cells (for example, 0) in the classification result res.

(vii) Step 1307

The plural-classification determination portion 13 repeats the processing from the above-described steps 1302 to 1306 in order to perform the one-classification determination portion 12 with respect to all of the types set in advance. By repeating steps 1302 to 1306, it is possible to determine whether the cells are normal cells or abnormal cells with respect to all of the types set in advance. In a case where it is determined that the cells are different types, the filter coefficient wj and the offset bi for the corresponding type are read from the memory, and the feature value fi which corresponds to the type is acquired. When it is determined that the determination of all of the types is finished, the processing moves to step 1308.

(viii) Step 1308

The drawing portion 14 draws the detection frame which indicates the abnormal cells on the image and displays the detection frame when pressing the image button illustrated in FIG. 7 with respect to the type determined as the abnormal cells. The drawing portion 14 does not draw the detection frame on the image when pressing the image button illustrated in FIG. 7 with respect to the type determined to be normal cells.

(ix) Step 1309

The storage portion 15 preserves the coordinate information for drawing the detection frame on the input target image by the drawing portion 14 and the target image in the memory 90 (corresponds to the storage device 203).

According to the second embodiment, by using the feature values of the plurality of direction components, by learning the deformed degree of the cells and by calculating the weight, the filter coefficient, and the offset, the discriminator which determines whether the cells are normal cells or abnormal cells is created, and thus, regarding the one-classification, it is possible to suppress misdetection or over-detection, and to classify the cells into normal cells or abnormal cells from one image.

In addition, by using the classification result by the discriminator of the plurality of one-classifications set in advance, in order to classify the tissues and cells, it is possible to perform determination of the probability of abnormal cells (for example, cancer) which corresponds to the degree of progress of abnormal cells (for example, cancer).

Furthermore, not by determining all of the classifications at once, but by determining whether or not the type corresponds to each of the classifications, it is possible to perform determination that the misdetection is suppressed.

(3) Third Embodiment

FIG. 14 is a functional block diagram illustrating a configuration of a remote diagnosis support system 1400 according to a third embodiment of the present invention. The remote diagnosis support system 1400 includes a server 1403 and an image obtaining apparatus 1405.

The image obtaining apparatus 1405 is an apparatus, such as a virtual slide apparatus or a personal computer equipped with a camera, and includes a capturing portion 1401 which captures the image data, and a display portion 1404 for displaying the determination result which has been transmitted from the server or the like 1403. In addition, although not being illustrated, the image obtaining apparatus 1405 includes a communication device which sends the image data to the server or the like 1403 and receives the data that has been sent from the server or the like 1403.

The server or the like 1403 includes the image processing apparatus 1 which performs the image processing according to the first or second embodiment of the present invention, with respect to the image data that has been transmitted from the image obtaining apparatus 1405, and a storage portion 1402 which stores the determination result output from the image processing apparatus 1. In addition, although not being illustrated, the server or the like 1403 includes a communication device which receives the image data that has been sent from the image obtaining apparatus 1405, and sends the determination result data to the image obtaining apparatus 1405.

The image processing apparatus 1 determines whether or not the cells are normal cells or abnormal cells for each type of the abnormal cells (for example, cancer), with respect to the cells in the image data captured by the capturing portion 1401. In addition, by using the classification result by the discriminator of the plurality of one-classifications set in advance, the determination of the probability of abnormal cells (for example, cancer) which corresponds to the degree of progress of abnormal cells (for example, cancer) is performed. The display portion 1404 displays the determination result transmitted from the server or the like 1403 to a display screen of the image obtaining apparatus 1405.

As the image obtaining apparatus 1405, a regenerative medicine apparatus or a culture apparatus of iPS cells including the capturing portion, or an MRI or an ultrasonic image capturing apparatus, may be used.

According to the third embodiment, with respect to the cells in the image transmitted from the facilities or the like at different locations, by determining whether the cells are normal cells or abnormal cells, by transmitting the determination result to the facilities or the like at different locations, and by displaying the determination result by the display portion of the image obtaining apparatus at the facilities or the like, it is possible to provide the remote diagnosis support system.

(4) Fourth Embodiment

FIG. 15 is a functional block diagram illustrating a configuration of a net entrusting service providing system 1500 according to a fourth embodiment of the present invention. The net entrusting service providing system 1500 includes a server or the like 1503 and an image obtaining apparatus 1505.

The image obtaining apparatus 1505 is an apparatus, such as a virtual slide apparatus or a personal computer equipped with a camera, and includes a capturing portion 1501 which captures the image data, a storage portion 1504 which stores the discriminator transmitted from the server or the like 1503, and the image processing apparatus 1 which reads the discriminator transmitted from the server or the like 1503, and performs the image processing according to the second embodiment of the present invention for determining whether the cells are normal cells or abnormal cells with respect to the cells in the image that is newly captured by the capturing portion 1501 of the image obtaining apparatus 1505. In addition, although not being illustrated, the image obtaining apparatus 1505 includes a communication device which sends the image data to the server 1503 or the like and receives the data that has been sent from the server or the like 1503.

The server or the like 1503 includes the image processing apparatus 1 which performs the image processing according to the second embodiment of the present invention, with respect to the image data that has been transmitted from the image obtaining apparatus 1505, and a storage portion 1502 which stores the discriminator output from the image processing apparatus 1. In addition, although not being illustrated, the server or the like 1503 includes a communication device which receives the image data that has been sent from the image obtaining apparatus 1505, and sends the discriminator to the image obtaining apparatus 1505.

The image processing apparatus 1 performs the machine learning so as to determine that the normal cells are normal cells or that the abnormal cells are abnormal cells with respect to the cells in the image data captured by the capturing portion 1501, and creates the discriminator which is adapted to the image of the facilities of the like at different locations.

The storage portion 1504 stores the discriminator or the like transmitted from the server or the like 1503.

The image processing apparatus 1 in the image obtaining apparatus 1505 reads the discriminator or the like from the storage portion 1504, determines whether the cells are normal cells or abnormal cells with respect to the cells in the image that is newly captured by the capturing portion 1501 of the image obtaining apparatus 1505 by using the discriminator, and displays the determination result on the display screen of the output device 204 of the image processing apparatus 1.

As the image obtaining apparatus 1505, a regenerative medicine apparatus or a culture apparatus of iPS cells including the capturing portion, or an MRI or an ultrasonic image capturing apparatus, may be used.

According to the fourth embodiment, with respect to the cells in the image transmitted from the facilities or the like at different locations, by creating the discriminator or the like by performing the machine learning so as to determine that the normal cells are normal cells and the abnormal cells are abnormal cells, by transmitting the discriminator or the like to the facilities or the like at different locations, by reading the discriminator by the image obtaining apparatus in the facilities or the like, and by determining whether the cells are normal cells or the abnormal cells with respect to the cells in the image which is newly captured, it is possible to provide the net entrusting service providing system.

(5) Conclusion (i) The image processing apparatus of the first embodiment according to the present invention executes the processing of calculating the feature values of the plurality of direction components, processing of acquiring the variance value which indicates the deformed degree of the cells, processing of classifying the cells into normal cells or abnormal cells from one image with respect to the one-classification, and processing of classifying the tissues and cells by using the classification result of the plurality of one-classifications set in advance and determining the probability of abnormal cells (for example, cancer) which corresponds to the degree of progress of abnormal cells (for example, cancer). More specifically, as illustrated in Equation 1, the feature values of the plurality of direction components are acquired, and as illustrated in Equations 2 and 3, by using the feature value fi of the plurality of direction components, the variance value var which indicates the deformed degree of the cells is acquired. When acquiring the feature value fi, not by using the filter in the plurality of directions, but by rotating the target image in the plurality of directions, the feature value fi may be acquired. The calculated variance value var shows the uniformity of the cells, and it is possible to classify the cells into normal cells or abnormal cells from the variance value.

In addition, since the probability of abnormal cells (for example, cancer) is determined by classifying the tissues and cells by using the classification result of the plurality of one-classifications set in advance, it is possible to display the determination result which corresponds to the degree of progress of abnormal cells (for example, cancer).

(ii) The image processing apparatus of the second embodiment executes the processing of performing the machine learning with respect to the deformed degree of the cells by acquiring the feature values of the plurality of direction components and using the acquired feature values, processing of classifying the cells into normal cells or abnormal cells from one image regarding the one-classification by using the discriminator acquired by the machine learning, and processing of classifying the tissues and cells by using the classification result of the plurality of one-classifications set in advance, and determining the probability of abnormal cells (for example, cancer) which corresponds to the degree of progress of abnormal cells (for example, cancer). More specifically, as illustrated in Equation 1, the feature values of the plurality of direction components are acquired, and as illustrated in Equations 4 and 5, the weight of the discriminator, the filter coefficient, and the offset are calculated by performing the machine learning with respect to the deformed degree of the cells so as to determine that the normal cells are normal cells and the abnormal cells are abnormal cells. In addition, by using the weight of the discriminator, the filter coefficient, and the offset which are acquired by the machine learning, with respect to the cells in the input image desired to be determined, regarding one-classification, it is possible to classify whether the cells are normal cells or abnormal cells from one image. Furthermore, since the tissues and cells are classified by using the classification result of the plurality of one-classifications set in advance, the probability of abnormal cells (for example, cancer) which corresponds to the degree of progress of abnormal cells (for example, cancer) is determined, and thus, it is possible to display the determination result which corresponds to the degree of progress of abnormal cells (for example, cancer).

(iii) According to the third embodiment, with respect to the cells in the image transmitted from the facilities or the like at different locations, by determining whether the cells are normal cells or abnormal cells, and by displaying the determination result in the display portion of the image obtaining apparatus at the facilities at different locations, it is possible to provide the remote diagnosis support system.

(iv) According to the fourth embodiment, with respect to the cells in the image transmitted from the facilities or the like at different locations, by creating the discriminator or the like by performing the machine learning so as to determine that the normal cells are normal cells and the abnormal cells are abnormal cells, by reading the discriminator by the image obtaining apparatus at the facilities or the like at different locations, and by determining the cells into normal cells or abnormal cells with respect to the cells in the image which is newly captured, it is possible to provide the net entrusting service providing system.

(v) With respect to each of the above-described embodiments, the following changes are possible.

In the feature extracting portion 11 or the learning portion 16, the feature values of the plurality of direction components are acquired by using the filter illustrated in FIG. 3, but other feature values, such as HOG, may be used, and similar effects can be achieved.

In the one-classification determination portion 12, the machine learning is performed with respect to the deformed degree of the cells by using the logistic regression, but linear regression or Poisson regression may be used, and similar effects can be achieved.

In the one-classification determination portion 12, the classification determination of the cells is performed by using the variance value of the plurality of direction components or by using the machine learning, but both of the determination result by the variance value of the plurality of direction components and the determination result by the machine learning may be used, and similar effects can be achieved.

(vi) The present invention can also be realized by a program code of software that realizes the function of the embodiment. In this case, the storage medium that stores the program code therein is provided in a system or a device, and the computer (or CPU or MPU) of the system or the apparatus reads the program code stored in the storage medium. In this case, as the program code itself read from the storage medium realizes the functions of the above-described embodiments, the program code itself and the storage medium which stores the program code therein configure the present invention. Examples of the storage medium for supplying the program code include a flexible disk, a CD-ROM, a DVD-ROM, a hard disk, an optical disk, a magneto-optical disk, a CD-R, a magnetic tape, a non-volatile memory card, and a ROM.

In addition, based on the instruction of the program code, as an operating system (OS) that is driven on the computer or the like performs a part or the entirety of the practical processing, the functions of the above-described embodiments may be realized by the processing. Furthermore, after the program code read from the storage medium is written in the memory on the computer, based on the instruction of the program code, the CPU or the like of the computer may perform a part or the entirety of the practical processing, and the functions of the above-described embodiments may be realized by the processing.

Furthermore, by delivering the program code of the software that realizes the functions of the embodiments via the network, the program code is stored in storage means, such as the hard disk or the memory, or the storage medium, such as the CD-RW or CD-R in the system or the apparatus, and the computer (or CPU or MPU) of the system or the apparatus which is in use may read and execute the program code stored in the storage means or the storage medium.

Finally, the process and the technology described here are essentially not related to any specific device, and can also be implemented by any corresponding combination of the components. Furthermore, multiple types of general-purpose devices can be used according to the method described here. In executing the steps of the method described here, there is also a case where it is advantageous to build the dedicated apparatus. In addition, by appropriately combining the plurality of configuration elements with each other disclosed in the embodiment, it is possible to form various inventions. For example, several configuration elements may be removed from all of the configuration elements described in the embodiment. Furthermore, the configuration elements which achieve different embodiments may be appropriately combined with each other. The present invention is described being associated with specific examples, but the specific examples are not for limitation in all the viewpoints but for the description. Those skilled in the art in the field definitely understand that there are multiple appropriate combinations of hardware, software, and firmware in realizing the present invention. For example, the above-described software can be implemented by a wide range of programs or script languages, such as assembler, C/C++, Perl, Shell, PHP, and Java (registered trademark).

Furthermore, in the above-described embodiment, control lines or information lines which are considered to be necessary for the description are illustrated, and the control lines or information lines do not necessarily illustrate all of the control lines or information lines for the product. All of the configurations may be connected to each other.

Additionally, other implementations of the present invention are apparent for those having general knowledge in the field by considering the specification and the embodiments of the present invention disclosed here. Various aspects and/or components of the described embodiments can be used independently or can be combined in any manner.

REFERENCE SIGNS LIST

1 IMAGE PROCESSING APPARATUS
10 INPUT PORTION
11 FEATURE EXTRACTING PORTION

12 ONE-CLASSIFICATION DETERMINATION PORTION
13 PLURAL-CLASSIFICATION DETERMINATION PORTION
14 DRAWING PORTION
15 STORAGE PORTION
16 LEARNING PORTION
90 MEMORY
91 CONTROL PORTION
201 CPU
202 MEMORY
203 STORAGE DEVICE
204 OUTPUT DEVICE
205 INPUT DEVICE
206 COMMUNICATION DEVICE
1400 REMOTE DIAGNOSIS SUPPORT SYSTEM
1500 NET ENTRUSTING SERVICE PROVIDING SYSTEM

The invention claimed is:

1. A cytologic diagnosis support apparatus that improves classification of abnormal cells, the apparatus comprising:
an input that receives a target image of potentially abnormal cells;
a memory;
a processor that is communicatively coupled to the input and the memory; wherein the processor is configured to: rotate the target image by a predetermined amount a predetermined number of times to form a plurality of rotated images,
determine a plurality of feature values for the plurality of rotated images, wherein each of the plurality of feature values corresponds to a respective rotated image from the plurality of rotated images,
calculate a variance of the plurality of feature values between the plurality of rotated images,
perform a comparison of the variance of the plurality of feature values between the plurality of rotated images and a threshold, and
determine a final determination result that indicates whether or not the target image corresponds to one-classification based on the comparison.

2. The cytologic diagnosis support apparatus according to claim 1,
wherein the plurality of feature values are determined by applying an image filter.

3. The cytologic diagnosis support apparatus according to claim 1,
wherein the threshold is acquired by performing machine learning with respect to previously classified images.

4. The cytologic diagnosis support apparatus according to claim 1, wherein the processor is further configured to:
display the final determination result.

5. A cytologic diagnosis support method that improves classification of abnormal cells, the method comprising:
receiving, by a processor, a target image of potentially abnormal cells;
rotating, by the processor, the target image by a predetermined amount a predetermined number of times to form a plurality of rotated images;
determining, by the processor, a plurality of feature values for the plurality of rotated images, wherein each of the plurality of feature values corresponds to a respective rotated image from the plurality of rotated images;
calculating, by the processor, a variance of the plurality of feature values between the plurality of rotated images;
performing, by the processor, a comparison of the variance of the plurality of feature values between the plurality of rotated images and a threshold; and
determining a final determination result that indicates whether or not the target image corresponds to one-classification based on the comparison.

6. The cytologic diagnosis support method according to claim 5,
wherein the plurality of feature values are determined by applying an image filter.

7. The cytologic diagnosis support method according to claim 5,
wherein the threshold is acquired by performing machine learning with respect to previously classified images.

8. The cytologic diagnosis support method according to claim 5, further comprising:
displaying, by the processor, the final determination result.

9. The cytologic diagnosis support apparatus according to claim 1, wherein:
the input receives the target image from an imager that is located at a remote location; and
the processor further sends the determination result to a display located at the remote location.

* * * * *